US012661456B2

(12) United States Patent
Alexandersson

(10) Patent No.: US 12,661,456 B2
(45) Date of Patent: Jun. 23, 2026

(54) CAP FOR A MEDICAMENT DELIVERY DEVICE

(71) Applicant: SHL MEDICAL AG, Zug (CH)

(72) Inventor: Oscar Alexandersson, Haninge (SE)

(73) Assignee: SHL Medical AG, Zug (CH)

( * ) Notice: Subject to any disclaimer, the term of this patent is extended or adjusted under 35 U.S.C. 154(b) by 1086 days.

(21) Appl. No.: 17/774,270

(22) PCT Filed: Oct. 30, 2020

(86) PCT No.: PCT/EP2020/080523
§ 371 (c)(1),
(2) Date: May 4, 2022

(87) PCT Pub. No.: WO2021/094106
PCT Pub. Date: May 20, 2021

(65) Prior Publication Data
US 2022/0387729 A1     Dec. 8, 2022

(30) Foreign Application Priority Data
Nov. 13, 2019     (EP) .................................... 19208801

(51) Int. Cl.
*A61B 17/11*          (2006.01)
*A61M 5/32*           (2006.01)
(52) U.S. Cl.
CPC ................................. *A61M 5/3204* (2013.01)
(58) Field of Classification Search
CPC ............... A61B 17/11; A61M 25/0662; A61M 2025/0681; A61M 29/00
See application file for complete search history.

(56) References Cited

U.S. PATENT DOCUMENTS 9,072,833 B2     7/2015  Jennings et al.
2010/0016793 A1   1/2010  Jennings et al.
(Continued)

FOREIGN PATENT DOCUMENTS

EP          2468328 A1     6/2012
EP          2175917 B1     6/2013
(Continued)

OTHER PUBLICATIONS

International Search Report and Written Opinion for Int. App. No. PCT/EP2020/080523, mailed Feb. 18, 2021.

*Primary Examiner* — Bhisma Mehta
*Assistant Examiner* — Haden Matthew Ritchie
(74) *Attorney, Agent, or Firm* — McDonnell Boehnen Hulbert & Berghoff LLP

(57) ABSTRACT

A cap for a medicament delivery device is presented having a cap body and a medicament delivery member shield remover arranged in the cap body. The medicament delivery member shield remover has a tubular body extending along an axis in an axial direction from a proximal end to a distal end and extending in a circumferential direction around the axis, a slit in the tubular body extending in the axial direction, and a first protruding element extending from the tubular body towards the axis, and a second protruding element. The second protruding element has two protrusions extending from the tubular body away from the axis. The two protrusions are arranged on opposite sides of the slit in the circumferential direction. The cap body has a tubular body extending in the axial direction with a slit extending in the axial direction and having a tapered portion that tapers towards the distal end.

13 Claims, 4 Drawing Sheets

(56)           References Cited

U.S. PATENT DOCUMENTS

| | | | |
|---|---|---|---|
| 2010/0152659 | A1 | 6/2010 | Streit et al. |
| 2017/0246403 | A1 | 8/2017 | Cowe et al. |
| 2018/0369495 | A1 | 12/2018 | Stewart et al. |

FOREIGN PATENT DOCUMENTS

| | | | | | |
|---|---|---|---|---|---|
| EP | 2869872 | A1 | 5/2015 | | |
| EP | 2878322 | A1 | 6/2015 | | |
| EP | 2886144 | A1 | 6/2015 | | |
| EP | 3222313 | A1 | 9/2017 | | |
| EP | 2175915 | B1 | 2/2018 | | |
| EP | 3305348 | A2 | 4/2018 | | |
| EP | 3320932 | A1 | 5/2018 | | |
| WO | 2007/131013 | A1 | 11/2007 | | |
| WO | 2009/019437 | A1 | 2/2009 | | |
| WO | 2009/019440 | A1 | 2/2009 | | |
| WO | 2010/108116 | A1 | 9/2010 | | |
| WO | 2012/022810 | A1 | 2/2012 | | |
| WO | 2012/122643 | A1 | 9/2012 | | |
| WO | 2013/058697 | A1 | 4/2013 | | |
| WO | 2014/009705 | A1 | 1/2014 | | |
| WO | 2015/110532 | A1 | 7/2015 | | |
| WO | WO-2017223354 | A1 * | 12/2017 | .......... | A61M 5/3213 |
| WO | 2018/069031 | A1 | 4/2018 | | |
| WO | 2018/202458 | A1 | 11/2018 | | |
| WO | WO-2019091626 | A1 * | 5/2019 | .......... | A61M 5/3202 |

* cited by examiner

CAP FOR A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2020/080523 filed Oct. 30, 2020, which claims priority to European Patent Application No. 19208801.1 filed Nov. 13, 2019_. The entire disclosure contents of these applications are herewith incorporated by reference into the present application.

TECHNICAL FIELD

The present disclosure relates to caps for medicament delivery devices, and in particular to caps with needle shield removers.

BACKGROUND

Medicament delivery devices such as auto-injectors commonly have a number of components, one of which is a cap with a needle shield remover. The needle shield remover is typically provided to remove a needle shield from a needle when a cap is removed from the medicament delivery device. An example of a prior art needle shield remover is provided in WO 2019/091626, which provides a needle shield remover that can be created from a sheet of metal, thereby allowing for reduced production costs.

It has been appreciated that further improvements could be made in needle shield remover design, for example so as to provide a needle shield that is easier to incorporate into a medicament delivery device during manufacture when compared to previous designs.

SUMMARY

The present disclosure is defined in the appended claims, to which reference should now be made.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the term "longitudinal", "longitudinally", "axially" or "axial" refer to a direction extending from the proximal end to the distal end, typically along the device or components thereof in the direction of the longest extension of the device and/or component.

Similarly, the terms "transverse", "transversal", "transversally" refer to a direction generally perpendicular to the longitudinal direction.

An aspect of the disclosure concerns a medicament delivery member shield remover for a medicament delivery device, the medicament delivery member shield remover comprising a tubular body extending along an axis in an axial direction from a proximal end to a distal end and extending in a circumferential direction around the axis, a slit in the tubular body extending in the axial direction, a first protruding element extending from the tubular body towards the axis, and a second protruding element, wherein the second protruding element comprises two protrusions (18, 19) extending from the tubular body (12) away from the axis (20), and wherein the two protrusions (18, 19) are arranged on opposite sides of the slit (14) in the circumferential direction (28).

Another aspect of the disclosure concerns a cap for a medicament delivery device, the cap comprising a cap body and a medicament delivery member shield remover arranged in the cap body, wherein the medicament delivery member shield remover comprises a tubular body extending along an axis in an axial direction from a proximal end (first end) to a distal end (second end) and extending in a circumferential direction around the axis, a slit in the tubular body extending in the axial direction, a first protruding element extending from the tubular body towards the axis, and a second protruding element, wherein the second protruding element comprises two protrusions extending from the tubular body away from the axis, and wherein the two protrusions are arranged on opposite sides of the slit in the circumferential direction; wherein the cap body comprises a tubular body extending in the axial direction from a proximal end to a second end, and a slit in the tubular body extending in the axial direction, and wherein the slit comprises a tapered portion that tapers towards the distal end of the tubular body of the cap body; wherein the medicament delivery member shield remover is moveable in the axial direction relative to the cap body; and wherein the two protrusions of the medicament delivery member shield remover are arranged in the slit of the cap body.

A number of potential advantages may result from this new medicament delivery member shield remover when compared to previous medicament delivery member shield removers. For example, it can result in a reduction in the force required to insert the medicament delivery member shield into the medicament delivery member shield remover during assembly of the medicament delivery device. A medicament delivery member such as a needle shield remover can now grip more tightly on the RNS (rigid needle shield) at the point where the needle shield is removed, but not so hard prior to use. This can provide an improved device without affecting end user experience.

In one embodiment, the slit in the tubular body of the medicament delivery member shield remover extends in the axial direction from the distal end of the tubular body of the medicament delivery member shield remover. In one embodiment, the slit of the tubular body of the medicament delivery member shield remover extends at least 50% of the distance from the distal end of the tubular body of the medicament delivery member shield remover to the proximal end of the tubular body of the medicament delivery member shield remover. In one embodiment, the medicament delivery member shield remover extends at least 75% of the distance from the distal end of the tubular body of the medicament delivery member shield remover to the proximal end of the tubular body of the medicament delivery member shield remover.

In one embodiment, the slit of the tubular body of the medicament delivery member shield remover extends from the distal end of the tubular body of the medicament delivery member shield remover to the proximal end of the tubular body of the medicament delivery member shield remover.

This can provide a medicament delivery member shield remover that is easier to manufacture.

In one embodiment, the slit of the tubular body of the medicament delivery member shield remover is spaced apart from the distal end of the tubular body of the cap body.

In one embodiment, the two protrusions are arranged adjacent to the slit in the circumferential direction. In one embodiment, the two protrusions are both ribs and the ribs extend in the axial direction. In one embodiment, the medicament delivery member shield remover consists of only one slit in the circumferential direction.

In one embodiment, the first protruding element and/or at least a portion of each of the two protrusions are closer to the distal end of the tubular body of the medicament delivery member shield remover than the proximal end of the tubular body of the medicament delivery member shield remover. In one embodiment, the tubular body of the medicament delivery member shield remover has a circular cross-section but it is also feasible to have a non-circular cross section.

In one embodiment, the slit of the cap body extends from the proximal end of the tubular body of the cap body. This can make it easier to insert the medicament delivery member shield remover into the cap body. In one embodiment, the tapered portion is a U shape or a V shape. In one embodiment, the tapered portion (50) is spaced apart from the distal end of the tubular body of the cap body.

In one embodiment, the tapered portion is adjacent to the second protruding element in the axial direction. In such an embodiment, the second protruding element will start to enter the tapered portion as soon as the cap starts being removed from a medicament delivery device.

In one embodiment, the tapered portion is spaced apart from the second protruding element in the axial direction. In such an embodiment, the second protruding element will not start to enter the tapered portion until the cap has already been partially removed from a medicament delivery device. This means that the increased force required for the user to pull the cap off as a result of the force needed to pull the second protruding elements towards each other in the tapered portion and thereby grip on a medicament delivery member shield is not required until the cap is already partially removed, which can reduce the initial force required to start removing the cap from said medicament delivery device.

In one embodiment, the cap body comprises an inner cap body and an outer cap body. This can give more design flexibility to the shape of the inner cap body and can make it easier to assemble the cap, as the outer cap body can be arranged to prevent the medicament delivery member shield remover from falling out of the inner cap body. In one embodiment, the inner cap body is moveable in the axial direction relative to the outer cap body. This can improve user experience by reducing the initial force needed to start removing the cap.

Another aspect of the present disclosure concerns a medicament delivery device comprising a cap as described above. In one embodiment, the medicament delivery device is an auto-injector.

Another aspect of the present disclosure concerns a medicament delivery member shield remover for a medicament delivery device, comprising a tubular body extending along an axis in an axial direction from a proximal end to a distal end and extending in a circumferential direction around the axis, a slit in the tubular body extending in the axial direction from the distal end, a first protruding element extending from the tubular body towards the axis, and a second protruding element, wherein the second protruding element comprises two protrusions extending from the tubular body away from the axis, wherein the two protrusions are arranged adjacent to either side of the slit in the circumferential direction, and wherein at least a part of the second protruding element is spaced apart in the axial direction from the proximal end.

Another aspect of the present disclosure concerns a medicament delivery member shield remover for a medicament delivery device, comprising a tubular body extending along an axis in an axial direction from a proximal end to a distal end and extending in a circumferential direction around the axis, a slit in the tubular body extending in the axial direction from the distal end, a first protruding element extending from the tubular body towards the axis, and a second protruding element, wherein the second protruding element comprises two protrusions extending from the tubular body away from the axis, wherein the two protrusions are arranged on either side of the slit in the circumferential direction, and wherein at least a part of the second protruding element is spaced apart in the axial direction from the proximal end, wherein the medicament delivery member shield remover consists of only one slit in the circumferential direction.

In one embodiment of the medicament delivery member shield remover according to the third or fourth aspect of the present disclosure, the first protruding element is closer to the distal end than to the proximal end, and the second protruding element is closer to the distal end than to the proximal end.

Generally, all terms used in the claims are to be interpreted according to their ordinary meaning in the technical field, unless explicitly defined otherwise herein. All references to a/an/the element, apparatus, member, component, means, etc. are to be interpreted openly as referring to at least one instance of the element, apparatus, member component, means, etc., unless explicitly stated otherwise.

BRIEF DESCRIPTION OF THE DRAWINGS

Embodiments of the present disclosure will now be described by way of example only and with reference to the accompanying drawings, in which.

DETAILED DESCRIPTION

Figures 1, 2:
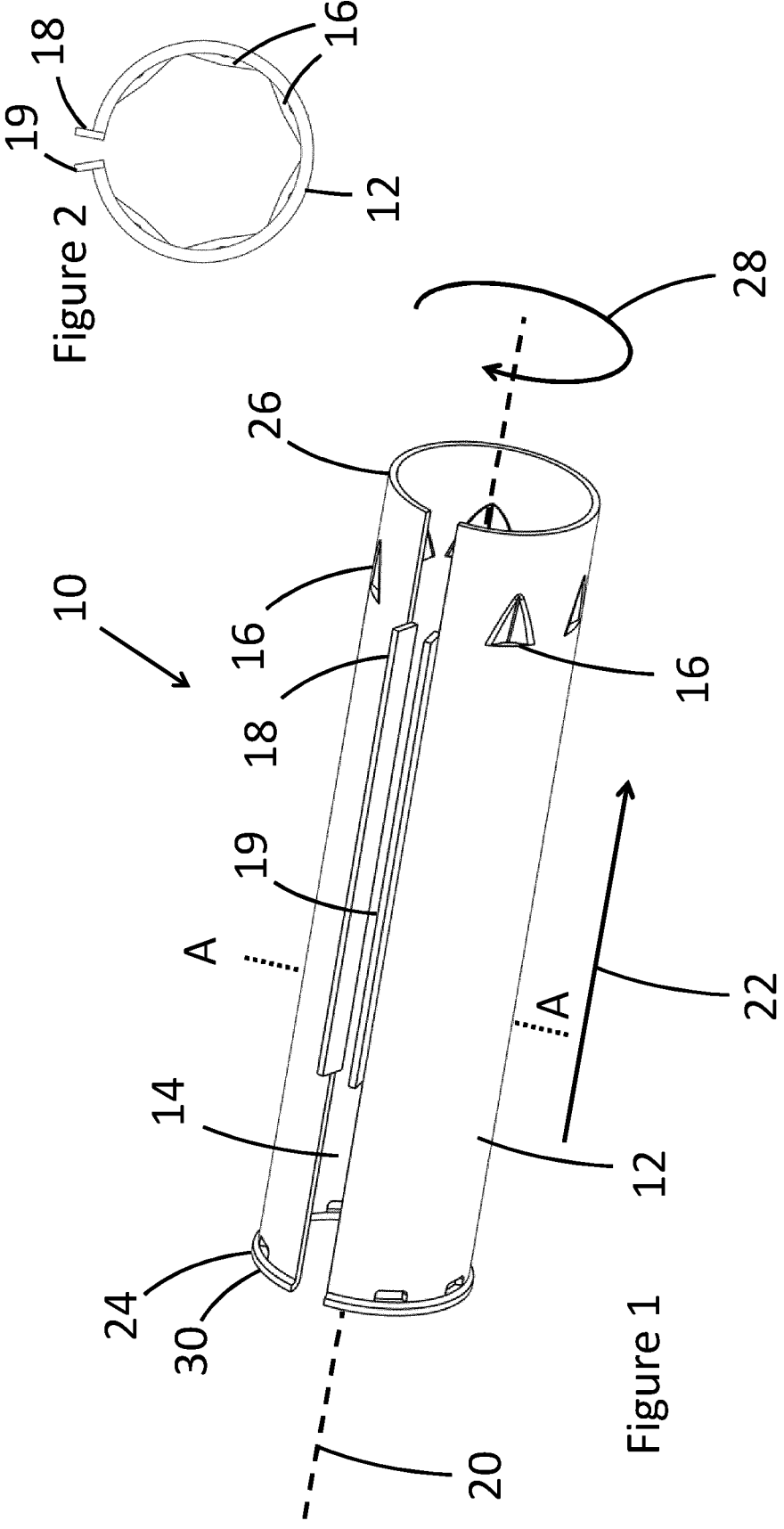
FIG. 1 shows a perspective view of a needle shield remover according to an embodiment of the present disclosure.
FIG. 2 shows a view of the needle shield remover of FIG. 1 perpendicular to the axis, from the plane A-A.

A needle shield remover 10 for a medicament delivery device is shown in FIGS. 1 and 2. The needle shield remover comprises a tubular body 12, a slit 14 in the tubular body 12, first protruding elements 16 and a second protruding element. The tubular body 12 extends along an axis 20 in an axial direction 22 from a proximal end 24 to a distal end 26 and extends in a circumferential direction 28 around the axis 20. A slit 14 in the tubular body 12 extends in the axial direction 22 from the distal end 26 of the tubular body 12 of the needle shield remover 10. A first protruding element 16 extends from the tubular body 12 towards the axis 20, and a second protruding element, which comprises two protrusions 18, 19, extends from the tubular body 12 away from the axis 20. The two protrusions 18, 19 are arranged on opposite sides of the slit 14 in the circumferential direction 28.

The embodiment in FIG. 1 shows the tubular body having the same radius at the proximal end 24 and the distal end 26, but alternatively the radius may vary along the tubular body in the axial direction. Also, although the tubular body is shown as having a circular cross-section when viewed parallel to the axis 20, a non-circular cross-section could also be used, depending for example on the shape of the needle shield that the needle shield remover is designed to engage.

The slit 14 in FIG. 1 extends in the axial direction from the proximal end 24 to the distal end 26. However, in other embodiments the slit may extend from the distal end and be spaced apart from the proximal end—in other words, the slit may extend for only part of the length of the tubular body from the distal end in the axial direction, rather than extending the entire length as shown in FIG. 1. For example, the slit may extend 50% to 75%, at least 50% or at least 75% of the distance from the distal end of the needle shield remover to the proximal end of the needle shield remover. The slit 14 is also shown in FIG. 1 with a constant width in the circumferential direction 28 from the proximal end to the distal end, but the width may vary in other embodiments. The embodiment in FIG. 1 only has one slit, but the tubular body of the needle shield remover can also have more than one slit.

The first protruding elements 16 extend from the tubular body 12 towards the axis 20. The first protruding elements 16 can engage a needle shield when the needle shield remover is in a medicament delivery device. The protruding elements may be punched out of the tubular body, as is shown in FIG. 1 (so the protruding elements could be an integral part of the tubular body), or they could alternatively be separate components added to the tubular body. In FIG. 1, the first protruding elements are shown as having a triangular shape when viewed from perpendicular to the axis 20. When viewed from parallel to the axis (as in FIG. 2), the protrusion of the first protruding elements from the tubular body 12 towards the axis 20 can be seen. The shape of the first protruding elements could also be varied. The primary intention of the first protruding elements is to grip onto a needle shield (typically a rigid needle shield) when incorporated in completed a medicament delivery device, as is described in more detail below.

The number of first protruding elements 16 in the example shown in FIG. 1 is six, but the first protruding elements could alternatively comprise one or more first protruding elements, with a total number of greater or less than six. The first protruding elements 16 would typically be closer to the distal end 26 than the proximal end 24.

The second protruding elements extend from the tubular body 12 away from the axis 20. The second protruding elements comprise protrusions 18, 19 on opposite sides of the slit 14 in the circumferential direction. In other words, the two protrusions comprise a first protrusion and a second protrusion, and the first protrusion is on one side of the slit in the circumferential direction and the second protrusion is on the other side of the slit in the circumferential direction. In the embodiment shown in FIG. 1, the second protruding elements are two ribs 18, 19, one on each side of the slit 14 in the circumferential direction, and the ribs extend in the axial direction 22. The second protruding elements are also spaced apart from both the proximal end 24 and the distal end 26. Various other shapes and locations are also possible for the second protruding elements. For example, the second protruding elements may extend to the proximal end and/or to the distal end of the tubular body 12. Alternatively or additionally, the second protruding elements may be spaced apart from the slit 14 in the circumferential direction 28, rather than being adjacent to the slit 14 as shown in FIG. 1. Although the second protruding elements on either side of the slit would typically each have the same structure, they could also be different from one another. The protruding elements may be separate components added to the tubular body, as shown in FIG. 1, or they may be an integral part of the tubular body. Although the second protruding elements shown in FIG. 1 extend in the axial direction about half the distance from the proximal end of the tubular body of the needle shield remover, the second protruding elements could also end further or less far in the axial direction. Instead of being ribs, the second protruding elements could also be another shape, for example a cylindrical shape with the longitudinal axis of the cylinder extending away from the tubular body. Typically, at least a part of the second protruding element is spaced apart in the axial direction from the proximal end of the tubular body 12.

When in use (or more specifically, when a cap containing the needle shield remover 10 is being removed from a medicament delivery device), the ribs are intended to interact with an inner portion of a cap arranged outside the needle shield remover (described in more detail below) to reduce the diameter of the needle shield remover and thereby cause the first protruding elements 16 to grip a needle shield that is arranged inside the needle shield remover. As a result, in some embodiments it is beneficial to have the ribs 18, 19 relatively near the first protruding elements 16 in the axial direction. Therefore, in some embodiments, at least a portion of each of the ribs 18, 19 is closer to the distal end 26 than the proximal end 24, and the first protruding elements 16 may also be closer to the distal end 26 than the proximal end 24. In some embodiments, at least a portion of each of the ribs 18, 19 is at the same position in the axial direction as the first protruding elements (i.e. at the same distance from the distal end). This may help increase the grip on the needle shield.

The needle shield remover 10 optionally comprises a flange 30 at the proximal end of the tubular body, as shown in FIG. 1. This can help hold the needle shield remover in place relative to other elements of the cap such as an inner cap body or an outer cap body as described below. The cut-outs shown in FIG. 1 in the tubular body of the needle shield remover adjacent to the flange are also optional.

Figures 3, 4:
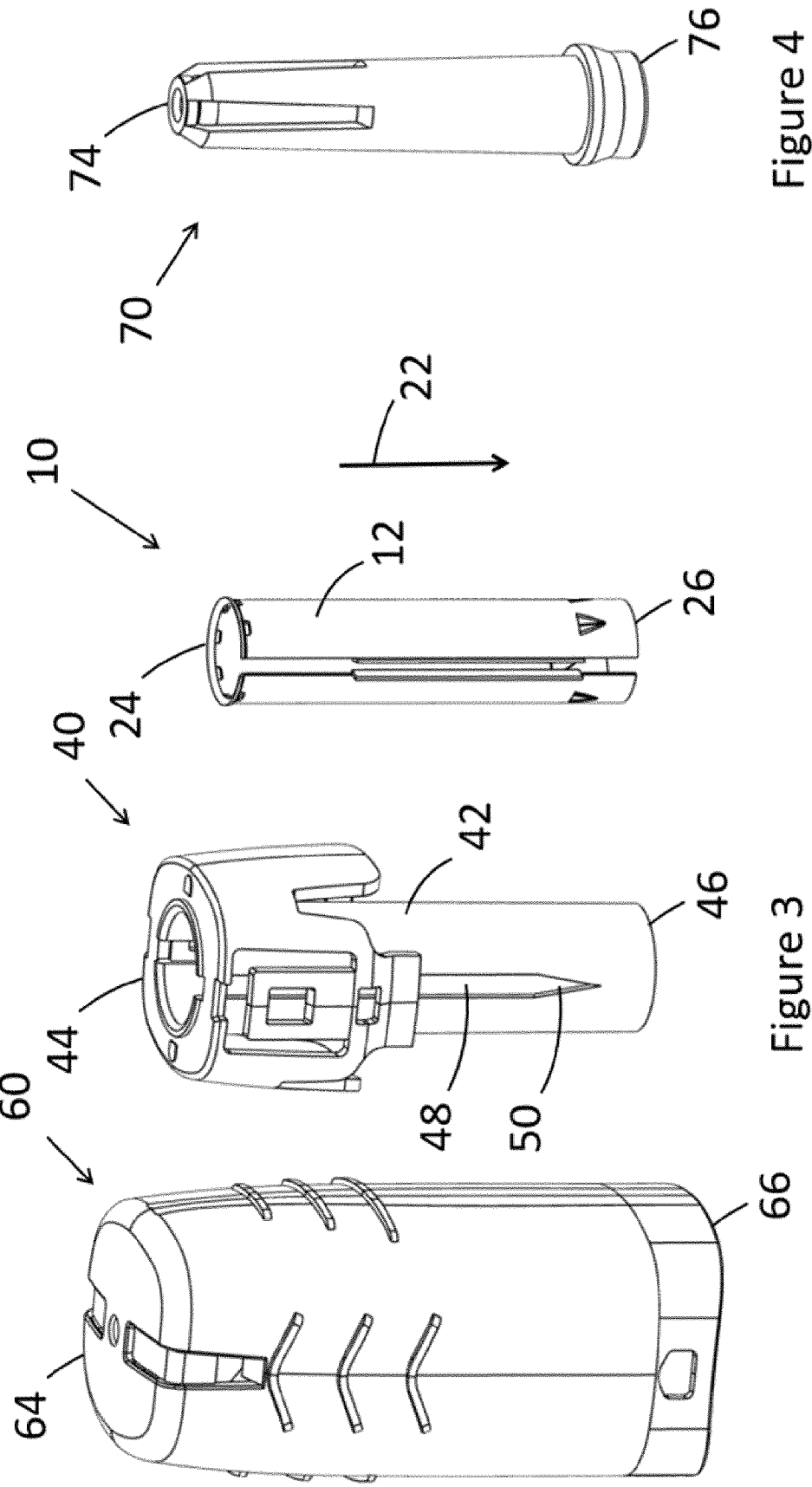
FIG. 3 shows a perspective view of the needle shield remover of FIG. 1, along with a cap according to an embodiment of the present disclosure.
FIG. 4 shows a perspective view of a needle shield.

The needle shield remover 10 is arranged in a cap body. FIG. 3 shows one embodiment of a cap comprising a cap body, and shows the needle shield remover 10 from the same angle for comparison. The cap body 40, 60 comprises a tubular body 42 extending in the axial direction 22 from a proximal end 24 to a distal end 26, and a slit 48 in the tubular body 42 of the cap body 40, 60, the slit 48 extending in the axial direction 22, wherein the slit 48 comprises a tapered portion 50. The needle shield remover 10 is moveable in the axial direction 22 relative to the cap body 40, 60, and the two protrusions 18, 19 of the needle shield remover 10 are arranged in the slit 48 of the cap body 40, 60.

The cap in the depicted embodiment comprises two pieces, namely an inner cap body 40 and an outer cap body 60. The inner cap body 40 comprises a tubular body 42 extending from a proximal end 44 to a distal end 46. The inner cap body also comprises a slit 48 in the tubular body 42, which extends in the axial direction and is spaced apart from the distal end 46. At a distal end of the slit 48 relative to the proximal end 44, the slit 48 comprises a tapered portion 50.

An outer cap body 60, which extends from a proximal end 64 to a distal end 66, is designed to fit over the inner cap body 40. The details of the precise shape of the outer cap body and the connection between the outer cap body and the inner cap body will not be fully described herein, but the outer cap body could be provided in various shapes and with various features; for example, the outer cap body could provide features such as a user-friendly grip and/or a clip to attach the cap to the rest of a medicament delivery device. Providing a separate outer cap body is also optional; as an alternative, a cap body may be provided that includes the desired features of both the inner cap body and the outer cap body shown in FIG. 3. The outer cap body may be fixed relative to the inner cap body, or may be free to move relative to the inner cap body in the axial direction.

As with the tubular body 12 of the needle shield remover, the embodiment of the inner cap body in FIG. 3 shows the tubular body 42 having the same internal radius at the proximal end 24 and the distal end 26, but alternatively the internal radius may vary along the tubular body in the axial direction. Also, although the tubular body is shown as having a circular cross-section perpendicular to the axis 20, a non-circular cross-section could also be used. The shape of the internal surface of the tubular body of the inner cap body would typically correspond to the shape of the external surface of the tubular body 12 of the needle shield remover.

The slit 48 would typically extend in the axial direction 22 from the proximal end 44, as shown in FIG. 3, although it may alternatively be spaced apart in the axial direction from the proximal end. Additionally or alternatively, the slit (or more specifically the tapered portion of the slit) may extend to the distal end in the axial direction, instead of being spaced apart from the distal end 46 in the axial direction 22, as shown in FIG. 3.

The tapered portion 50 of the slit 48 is shown as V shaped in FIG. 3. Alternatively, another shape could be used, such as a U shape. The tapered portion tapers towards the distal end; that is, the end of the tapered portion closest to the proximal end 44 is widest in the circumferential direction, and the end of the tapered portion furthest from the proximal end 44 is narrowest in the circumferential direction. The tapered portion would typically be the portion of the slit closest to the distal end 46.

When a cap is provided from the parts above, complete with a needle shield remover, the needle shield remover is moveable in the axial direction relative to the cap body. The needle shield remover 10 may be aligned in the inner cap body 40 so that the second protruding elements are adjacent to the tapered portion 50 in the axial direction. In such an embodiment, the grip of the needle shield remover would tighten on an associated needle shield as soon as the needle shield remover 10 moves relative to the inner cap body 40. Alternatively, the second protruding elements can be spaced apart from the tapered portion in the axial direction. In such an embodiment, the needle shield remover does not start gripping harder on the needle shield immediately when a user starts removing the cap, as the second protruding elements would initially move down the slit 48 of the inner cap body until they reach the tapered portion 50. The needle shield is then only gripped more tightly after the inner cap body has moved a certain distance in the axial direction relative to the rest of a medicament delivery device (more specifically relative to the needle shield). For more context, operation of a medicament delivery device that contains a cap with a needle shield remover as described above is outlined in more detail below.

FIG. 4 shows an example of a needle shield 70. The needle shield 70 extends from a proximal end 74 to a distal end 76. In a completed medicament delivery device as described in more detail below, the needle shield 70 would be inside the needle shield remover 10.

Figure 5:
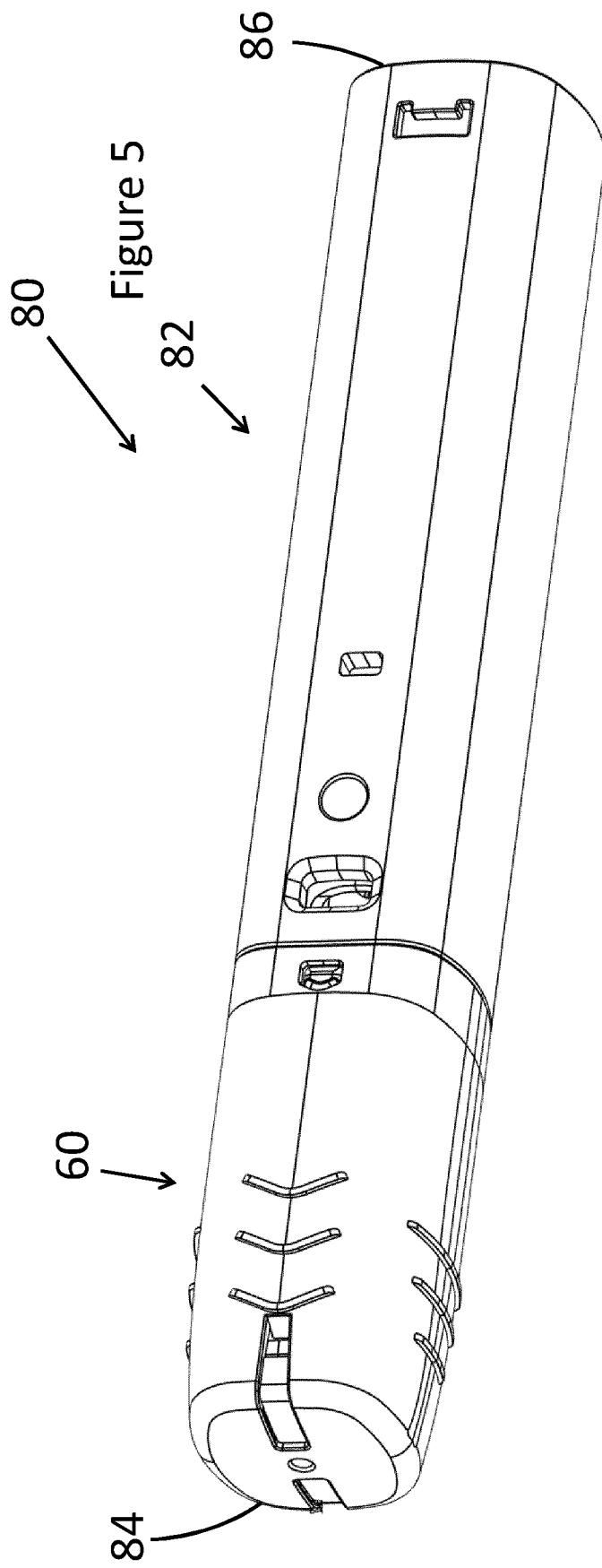
FIG. 5 shows a perspective view of a medicament delivery device that incorporates the cap of FIG. 3.
Figure 6:
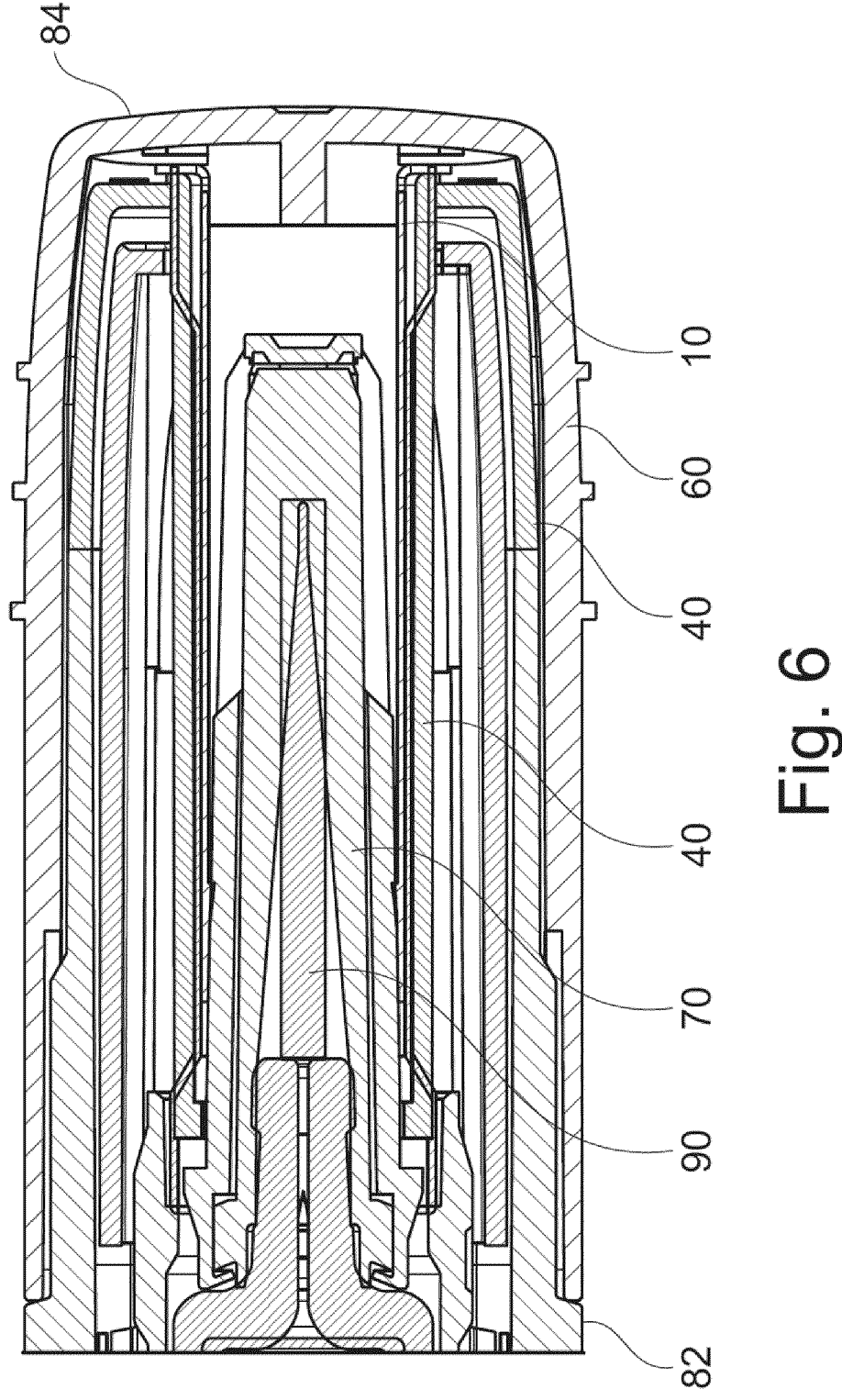
FIG. 6 shows a cross-section of a front (proximal) part of the medicament delivery device of FIG. 5, including the cap.

A cap such as that described above can be used as a component of a medicament delivery device such as an auto-injector. In general, various shapes and types of medicament delivery device could be used with the cap described above and/or the needle shield remover described above, and an embodiment of one such medicament delivery device is provided in FIG. 5. FIG. 5 shows a medicament delivery device 80 extending from a proximal end 84 to a distal end 86. In this view, the outer cap body 60 and an outer housing 82 of the medicament delivery device are visible. FIG. 6 shows a cross-section of a portion of the medicament delivery device of FIG. 5, in which the needle shield remover 10, the inner cap body 40, the outer cap body 60 and the outer housing 82 are visible, along with the needle shield 70. Other features such as the needle 90 are also visible. The medicament delivery device would also include, among other components, a medicament container inside the outer housing 82 and a powerpack assembly inside the outer housing 82. The medicament container comprises a medicament barrel and the needle 90 with a needle cover such as the needle shield 70 shown in FIG. 4. The needle cover shown in FIG. 4 is a rigid needle shield (RNS). In the embodiment of FIG. 6, the needle cover comprises two needle shields, namely a rigid needle shield and a flexible needle shield (FNS) inside the rigid needle shield, but alternatively the needle cover may only have one needle shield.

During manufacturing of a needle shield remover as described above, the needle shield remover may be made from a single sheet of material or from a tube, for example. The needle shield remover is normally made of a material that is harder than the material in the needle shield, and would typically be made of metal.

During assembly of a cap as described above, the needle shield remover 10 would typically first be inserted into the inner cap body 40, with the distal end 26 of the needle shield remover entering into the tubular body 42 of the inner cap body at the proximal end 44 of the inner cap body. The proximal end 44 of the inner cap body would then be inserted into the distal end 66 of the outer cap body 60. If the second protruding elements are adjacent to the tapered portion 50 in the axial direction, this restricts movement of the cap body (more specifically the inner cap body) relative to the needle shield remover before use of the device (for example in transit). If the second protruding elements are spaced apart from the tapered portion 50 in the axial direction, the needle shield remover could be arranged so that it is free to move in the axial direction relative to the inner cap body 40 before use of a medicament delivery device containing the cap (for example in transit).

During final assembly of a medicament delivery device incorporating a cap as described above, the medicament delivery device would typically initially be provided in several separate parts, which are then fitted together. During final assembly, the medicament container of the medicament delivery device is inserted into the cap. In particular, the needle shield (or, more specifically, the rigid needle shield in a design with both a flexible needle shield and a rigid needle shield) of the medicament container is inserted into the needle shield remover. The first protruding elements may already engage gently with the needle shield as a result of final assembly of the medicament delivery device, but providing a needle shield remover as outlined above means that they do not need to engage the needle shield so strongly, which can make it easier to insert the needle shield into the needle shield remover. This results in a medicament delivery device that is easier to assemble.

During use of the device, the user will remove the cap from the medicament delivery device. As the cap is pulled away from the rest of the medicament delivery device, the cap body 40, 60 will move in the axial direction 22 relative to the rest of the medicament delivery device. Once the second protruding elements engage the tapered portion 50, the grip of the first protruding elements 16 on the needle shield 70 will tighten (because the radius of the needle shield remover is reduced as the second protruding elements are pulled towards each other as the second protruding elements enter the tapered portion 50), and the needle shield will remain immovable relative to the needle shield remover in the axial direction, meaning that the needle shield remover will be removed from the medicament delivery device along with the cap. The medicament delivery device can subsequently be used to deliver an injection.

Throughout the application, various components have been described as having a proximal end and a distal end. These components could alternatively be described as extending from a first end to a second end. The proximal end is the end of the medicament delivery device (or of the individual component) that is closest to the dose delivery site in the axial direction 22 when the medicament delivery device is placed on the skin of a user in preparation for injecting a medicament from the medicament delivery device into the user. The examples in the application describe a needle shield, a needle shield remover, and so on. However, the present disclosure is applicable to medicament delivery members more generally and not just needles.

Various modifications to the embodiments described are possible and will occur to those skilled in the art without departing from the present disclosure which is defined by the following claims.

The invention claimed is:

1. A cap for a medicament delivery device, the cap comprising:
   a cap body; and
   a medicament delivery member shield remover arranged in the cap body, wherein the medicament delivery member shield remover comprises:
      a tubular body extending along an axis in an axial direction from a proximal end to a distal end and extending in a circumferential direction around the axis;
      a slit in the tubular body extending in the axial direction;
      a first protruding element extending from the tubular body towards the axis; and a second protruding element,
      wherein the second protruding element comprises two protrusions extending from the tubular body away from the axis,
   wherein the cap body comprises:
   a tubular body extending in the axial direction from a proximal end to a distal end; and
   a slit in the tubular body of the cap body, the slit extending in the axial direction, wherein the slit comprises a tapered portion that tapers towards the distal end of the tubular body of the cap body,
   wherein the medicament delivery member shield remover is moveable in the axial direction relative to the cap body; and
   wherein the two protrusions of the medicament delivery member shield remover are arranged in the slit of the cap body.

2. The cap of claim 1, wherein the slit in the tubular body of the medicament delivery member shield remover extends in the axial direction from the distal end of the tubular body of the medicament delivery member shield remover.

3. The cap of claim 1, wherein the slit of the tubular body of the medicament delivery member shield remover extends at least 50% of the distance from the distal end of the tubular body of the medicament delivery member shield remover to the proximal end of the tubular body of the medicament delivery member shield remover.

4. The cap of claim 1, wherein the two protrusions are arranged adjacent to the slit in the circumferential direction.

5. The cap of claim 1, wherein the two protrusions are ribs that extend in the axial direction.

6. The cap of claim 1, wherein the medicament delivery member shield remover consists of only one slit in the circumferential direction.

7. The cap of claim 1, wherein the first protruding element and/or at least a portion of each of the two protrusions is closer to the distal end of the tubular body of the medicament delivery member shield remover than to the proximal end of the tubular body of the medicament delivery member shield remover.

8. The cap of claim 1, wherein the slit of the cap body extends from the proximal end of the tubular body of the cap body.

9. The cap of claim 1, wherein the tapered portion is a U shape or a V shape.

10. The cap of claim 1, wherein the tapered portion is adjacent to the second protruding element in the axial direction.

11. The cap of claim 1, wherein the tapered portion is spaced apart from the second protruding element in the axial direction.

12. The cap of claim 1, wherein the cap body comprises an inner cap body and an outer cap body.

13. The cap of claim 12, wherein the inner cap body is moveable in the axial direction relative to the outer cap body.

\* \* \* \* \*